United States Patent [19]

Ranby et al.

[11] Patent Number: 5,021,346

[45] Date of Patent: Jun. 4, 1991

[54] SOLID PHASE REACTANT FOR INHIBITION AND REMOVAL OF SERINE PROTEASES AND METHOD OF USE

[75] Inventors: Mats G. Ranby; Hans Peterson, both of Umea, Sweden

[73] Assignee: Biopool International, Inc., New York, N.Y.

[21] Appl. No.: 62,782

[22] Filed: Jun. 15, 1987

[51] Int. Cl.[5] ........................ C12N 9/50; C12N 9/68; B07J 13/00

[52] U.S. Cl. .................................... 435/219; 435/217; 435/815; 252/315.3

[58] Field of Search ............... 435/219, 815, 213, 217; 252/315.3

[56] References Cited

PUBLICATIONS

Nakayama, T. et al. (1977), Anal. Biochem. 78, 165–170.

Gordon, S. G. et al. (1981), J. Clin. Invest. 67, 1665–1671.

Affinity Chromatography, Principles and Methods (1979), Pharmacia Fine Chemicals, pp. 33–34.

Gel Filtration, Theory and Practice (1982), Pharmacia Fine Chemicals, pp. 16–17.

Affinity Chromatography, Principals and Methods, (1979), Pharmacia Fine Chemicals, pp. 19, 27–29.

Stryer, L., *Biochemistry*, pp. 129–130 (1975).

Lehninger, A., *Principles of Biochemistry*, pp. 221–223 (1982).

Pharmacia Fine Chemicals, "Affinity Chromatography, Principles and Methods", at pp. 6–7 (Jun. 1979).

Sigma Chemical Company, "Sigma Chemica Company Catalogue", p. 411 (1990).

Millqvist et al., "An Affinity Gel for the Inhibition, Binding and Isolation of Serine Proteases", *Anal. Biochem.* 170, pp. 289–292 (1988).

*Primary Examiner*—Elizabeth C. Weimar
*Assistant Examiner*—Charles L. Patterson
*Attorney, Agent, or Firm*—Askew & Lunsford Jones

[57] ABSTRACT

An affinity gel for the isolation of serine proteases from a biological sample. The affinity gel is modified for specificity for serine proteases by coupling an organophosphorous compound to the gel. The reaction is carried out in two steps. The hydrophilic gel is reacted with a phosphoryl trifluoride and then the coupled gel is further reacted with an alcohol to form the organophosphorous compound.

5 Claims, 1 Drawing Sheet

SOLID PHASE REACTANT FOR INHIBITION AND REMOVAL OF SERINE PROTEASES AND METHOD OF USE

TECHNICAL FIELD

The present invention relates to an affinity gel for the isolation of serine proteases, and more particularly to an affinity gel which is coupled to an organophosphorous compound.

BACKGROUND OF THE INVENTION

Proteases are enzymes that hydrolyze peptide bonds which covalently link amino acids together to form proteins. The presence of proteases in biological samples often causes serious problems in protein purification and in long-term storage of protein samples. These proteases hydrolyze the peptide bonds of the proteins, creating new impurities during the protein purification procedure. Protease contamination in biological samples preserved for long-term storage often causes decomposition of the sample.

Many proteases are classified as "serine" proteases. This means that an unusually reactive serine is part of the active site in the protease enzyme. It is known that the unusually reactive serine in the active site of the protease can be specifically labelled with an organic fluorophosphate such as diisopropylphosphofluoridate (DIPF). Another name for DIPF is diisopropylfluorophosphate. The DIPF reacts with the serine in the active site to form an inactive diisopropylphosphoryl-enzyme complex, which, under most conditions, is stable. Examples of serine proteases which react with DIPF include, but are not limited to, trypsin, elastase, thrombin, and subtilisin. Kallikrein activity in an immunoglobulin preparation or plasmin activity in a prourokinase preparation are examples of common serine protease contamination.

Diisopropylfluorophosphate has been shown to be an effective inhibitor for many serine proteases. However, there are problems associated with the use of diisopropyl fluorophosphate. First, diisopropyl fluorophosphate is a hazardous chemical as identified by the National Research Council Committee on Hazardous Substances in the laboratory. Second, the inhibitory effect of diisopropyl fluorophosphate diminishes with time due to hydrolysis, causing eventual release of the active enzyme.

Affinity chromatography is a biochemical technique used to isolate certain proteins from complex mixtures such as blood or urine. This technique is based on the biochemical attraction of these proteins for certain molecules, commonly referred to ligands. Specific proteins are highly attracted to ligands such as the polysaccharide agarose, and strong bonds are formed when these proteins are allowed to contact the ligand molecules. The other proteins and substances within the mixture are not attracted to the ligand and may be separated from the protein/ligand complex by filtration, centrifugation or chromatographic techniques.

One example of an affinity-type separation is an affinity chromatography column. Ligand molecules that are specific for a particular type of protein, are bound to a support that is packed into a column. The mixture to be resolved, including the protein to be isolated, is introduced into one end of the column. The protein to be isolated becomes bound to the ligand as it passes through the column while the remaining substances in the mixture pass through the column without interaction with the ligand. The substances that were not bound to the ligand exit through the opposite end of the column by the force of gravity or by the use of a high-pressure pump. The ligand molecules remain stationary within the chromatography column during the separation procedure. The bound protein is then eluted from the column by rinsing the column with a solution which is capable of releasing the protein from the ligand.

Affinity gels can also be formed into a slab or rod for the electrophoretic separation of proteins based on relative ionic charge. Typical of these types of gels are polyacrylamide gels.

Thus, isolation of a particular protein from a biological sample by affinity chromatography depends upon the high affinity of the selected protein for the ligand and the lack of affinity between the other constituents of the sample and the ligand.

Consequently, there is a need for a safe and effective method of removing serine proteases from a biological sample to improve protein purification and to increase the storage potential for isolated protein samples.

SUMMARY OF THE INVENTION

In accordance with the present invention, a solid phase reactant is provided that is effective in removing serine proteases from a biological sample. The modified affinity gel of the present invention comprises organophosphorous groups coupled to a hydrophilic affinity gel matrix. This modified affinity gel provides a specific ligand for the binding and inactivation of serine proteases and has the following chemical formula:

Matrix-O-POF-OR wherein O represents oxygen, P represents phosphorous, F represents fluoride and R represents an alkyl group. The matrix can be any material with a hydroxyl group, such as agarose, dextran cellulose, hydroxyappetite or substituted polyacrylamide like Frisacryl I.B.F.

The present invention also includes a method for the modification of a gel matrix comprising the steps of (1) reacting a phosphoryl trifluoride with the affinity gel according to the following chemical equation:

$$\text{Matrix-OH} + POF_3 \rightarrow \text{Matrix-O-}POF_2 + HF$$

wherein the hydroxylated matrix is a hydrophilic affinity gel and F is a fluoride, so that the phosphoryl trifluoride is coupled to the affinity gel by electrophilic attack of the phosphoryl trifluoride to the hydroxyl groups on the hydrophilic gel, forming a matrix which is coupled to a phosphoryl difluoride, and (2) reacting the matrix coupled to the phosphoryl difluoride with a predetermined quantity of an alcohol according to the following chemical equation:

$$\text{Matrix-O-}POF_2 + ROH \rightarrow \text{Matrix-O-POF-OR} + HF$$

wherein R is a carbon chain and F is a fluoride, so that the carbon chain from the alcohol is bound to the coupled phosphoryl dihalide by nucleophilic attack of the alcohol to the phosphoryl fluoride. The affinity gel thus modified is capable of covalently binding to the active site of serine proteases.

A method for the removal of serine proteases from a biological sample is also provided. This method comprises coupling an organophosphorous compound to a hydrophilic affinity gel according to the following chemical equation:

$$Matrix\text{-}OH+POF_3 \rightarrow Matrix\text{-}O\text{-}POF_2+HF$$

$$Matrix\text{-}O\text{-}POF_2+ROH \rightarrow Matrix\text{-}O\text{-}POF\text{-}OR+HF$$

wherein the matrix is the hydrophilic affinity gel, F is fluoride and R is a carbon chain The affinity gel thus modified is then interacted with the biological sample so that the gel covalently binds to serine proteases in the biological sample.

Accordingly, it is an object of the present invention to provide an affinity gel that is specific for the binding of serine proteases.

Another object of the present invention is to provide a method for the removal of serine proteases from a biological sample.

Another object of the present invention is to provide a method for the removal of serine proteases from a biological sample which avoids the handling of hazardous chemicals.

These and other objects, features and advantages of the present invention will become apparent after a review of the following detailed description of the disclosed embodiment and the appended claims.

DETAILED DESCRIPTION OF THE DISCLOSED EMBODIMENT

Figure 1:
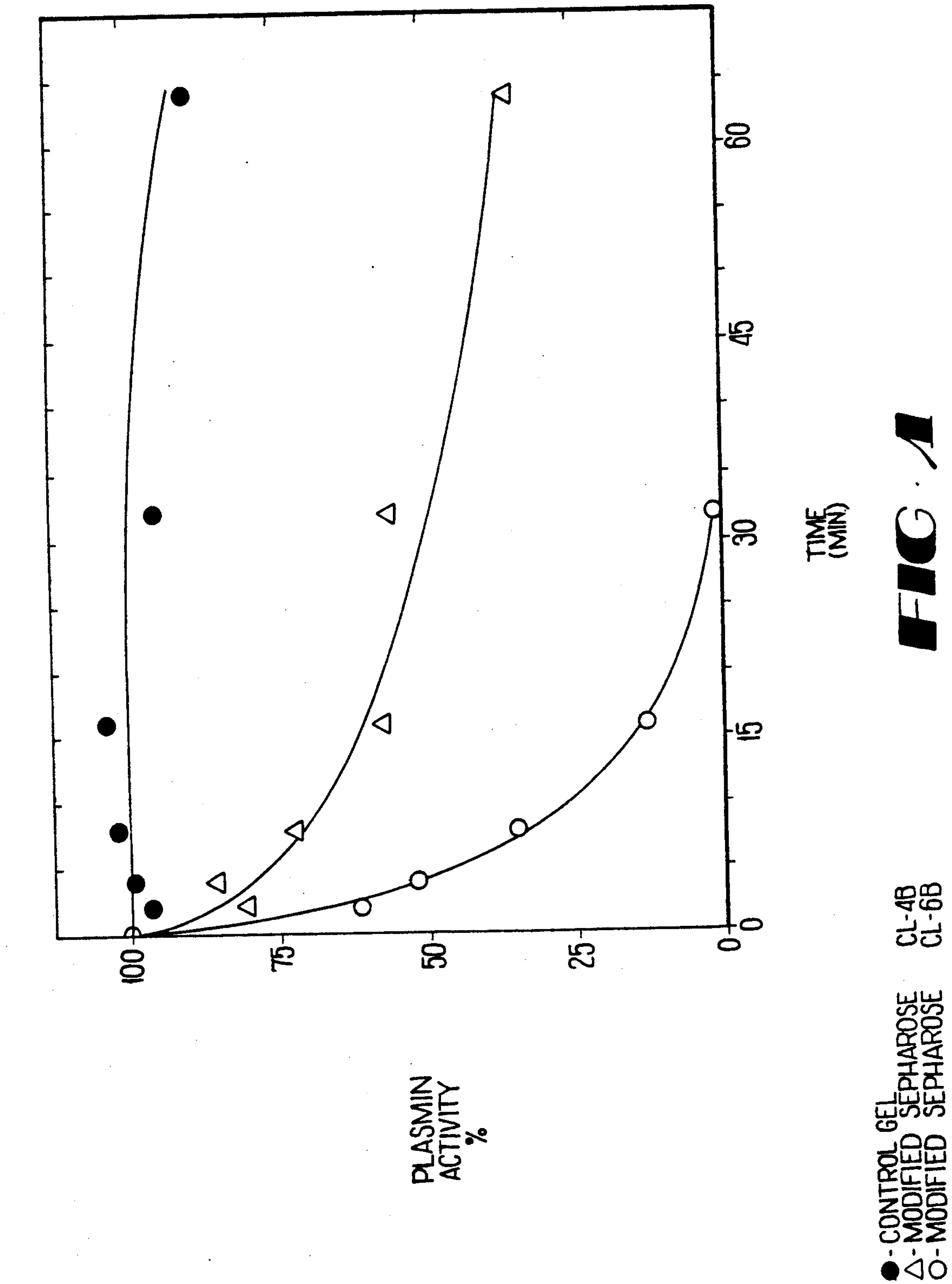
FIG. 1 is a graphical representation of the relative amount of plasmin inactivated by two embodiments of the present invention.

The present invention comprises a modified affinity gel and method for modifying an affinity gel so that the modified gel is coupled to molecules specific for the binding of serine proteases and comprises a method of removing serine proteases from biological samples. Several substances containing serine proteases that can be isolated from biological samples include, but are not limited to, chymotrypsin, trypsin, kallikrein, plasmin, thrombin and bathrombin.

The present invention comprises an affinity gel matrix modified with an organophosphorous compound. The modified gel has the following general formula:

$$Matrix\text{-}O\text{-}POF\text{-}OR$$

wherein the matrix is a hydrophilic affinity gel such as an agarose gel, F represents fluoride, and R is a carbon chain including approximately 1 to 12 carbon groups, with a preferable number of carbon groups being from 2 to 6 and most preferably three carbon groups.

The affinity gel matrix is first modified for serine protease specificity by coupling a phosphoryl trihalide, preferably phosphoryl trifluoride, to the gel matrix. The gel matrix is preferably a hydrophilic gel such as agarose. The matrix can also be any material with a hydroxyl group, such as dextran cellulose, hydroxyappetite or substituted polyacrylamide like Frisacryl I.B.F and Epoxy-activated Sepharose CL-6B affinity gel. Coupling is achieved by electrophilic attack of the phosphorous compound to the hydroxyl groups on the hydrophilic gel, forming a matrix coupled to a phosphoryl dihalide. The following formula demonstrates the first reaction:

$$Matrix\text{-}OH+POF_3 \rightarrow Matrix\text{-}O\text{-}POF_2+HF$$

wherein the hydroxylated matrix is a hydrophilic affinity gel, preferably agarose and F is a fluoride. Preferably the reaction time is approximately five to seven hours, the reaction takes place at a temperature between approximately −50° and −100° C., and the reaction takes place at a pressure below approximately 200 mmHg.

The affinity gel matrix coupled to the phosphoryl dihalide is then further modified by nucleophilic attack of an alcohol to the phosphoryl dihalide. A matrix bound to an organophosphorous compound is formed according to the following formula which demonstrates the second reaction:

$$Matrix\text{-}O\text{-}POF_2+ROH \rightarrow Matrix\text{-}O\text{-}POF\text{-}OR+HF$$

wherein R is a carbon chain including approximately 1 to 12 carbon groups, with a preferable number of carbon groups being from 2 to 6 and most preferably three carbon groups. The reaction time is approximately three to five hours, and the reaction takes place at a temperature between approximately 20° to 25° C.

The modified gel is washed with alcohol, preferably isopropanol, to remove the halide by-product, and the gel is stored in alcohol or is vacuum-dried for long-term storage. Alcohol is preferred over aqueous storage solutions because most organophosphorous compounds have limited stability in aqueous solutions. The gel is rehydrated with an aqueous buffer solution prior to usage. Buffers with low or high pH values should be avoided to minimize the degradation rate of the gel matrix during usage.

A one milliliter sample of the modified affinity gel matrix typically contains approximately 0.2 to 0.5 mmole of the phosphoryl halide substituted groups.

Interaction of the modified affinity gel with a biological sample containing serine proteases causes the serine proteases to covalently bind to the coupled organophosphorous compounds. The remaining components of the biological sample are not bound to the organophosphorous compounds and thus the serine proteases can be isolated from the biological sample by filtration, centrifugation, chromatography, electrophoresis or any other biochemical technique utilizing affinity gels.

EXAMPLE 1

Epoxy-activated Sepharose CL-6B affinity gel which is 6% epoxy-activated cross-linked agarose, (Pharmacia Biotechnology International AB, Uppsala, Sweden) is treated with 0.1 M sodium hydroxide for one hour on a vortex mixer to hydrolyze the epoxy groups to vicinal-diols. The treated gel is then washed with water until a neutral pH is reached. The gel is washed with acetone (P.A. quality, May & Baker Ltd, Dagenham, England) to remove the water and is stepwise equilibrated with anhydrous diethyl ether (P.A. quality, May & Baker Ltd, Dagenham, England). A suspension of two grams of the gel (dry weight) in 10 ml ether is placed in a closed teflon vessel with two outlets and is stirred slowly with a magnetic stirrer. The suspension is cooled to −75° C. in a dry ice/methanol bath and the air within the vessel is evacuated.

Phosphoryl trifluoride is synthesized according to the procedure of Lange and Livingston. (see Lange, E. and Livingston, R., *J. Am. Chem. Soc.,* 63, 1782–1789 (1941)). The reaction is carried out in an aluminum oxide tube (4×58 cm) with a rubber cap containing an outlet. The gaseous products are condensed and are distilled in gastight, Teflon® equipment, containing two 200 ml vessels, valves and a manometer, known as HF Reaction Apparatus Type IIA (Penisula Laboratories, Inc. Peptide Institute Inc. Minoh, Osaka, Japan). The phosphoryl trifluoride is condensed in a 1 liter gas cylinder of acid-resistant steel.

A needle valve is connected to the gas cylinder, and approximately two grams of the phosphoryl trifluoride is condensed into the ether suspension. The phosphoryl trifluoride is allowed to react with the hydroxyl groups of the gel according to the following reaction for six hours at a temperature of −75° C. and a pressure below 200 mm Hg:

$$Matrix\text{-}OH + POF_3 \rightarrow Matrix\text{-}O\text{-}POF_2 + HF$$

The gel is collected in a glass filter funnel and is washed extensively with cooled ether (−75° C.) to remove the unreacted phosphoryl trifluoride and the hydrogen fluoride by-product.

Because of the toxicity of phosphoryl trifluoride and hydrogen fluoride, it is important to treat the ether wash, containing phosphoryl trifluoride and hydrogen fluoride, according to the method set forth in the article *Prudent Practices for Handling Hazardous Chemical in Laboratories*, National Research Council. Committee on Hazardous Substances in the Laboratory, pp. 30–45, National Academy Press, Washington, D.C. (1981).

The modified gel is placed in a closed Teflon® vessel and is suspended in 20 ml of an ether/isopropanol (1/1) mixture (both the ether and the isopropanol being of P.A. quality, May & Baker Ltd, Dagenham, England). The suspension is reacted for four hours while being continuously stirred at room temperature (approximately 22° C.). The gel is collected on a glass filter funnel and is extensively washed with isopropanol to remove the hydrogen fluoride by-product. All isopropanol is collected and treated with sodium hydroxide to hydrolyze any diisopropyl fluorophosphate that might be formed according to the procedure of Lange and Livingston cited above. The affinity gel is then vacuum-dried for long-term storage.

EXAMPLE 2

Sepharose CL-4B affinity gel, which is 4% cross-linked agarose (Pharmacia Biotechnology International AB, Uppsala, Sweden) is washed with ten volumes of water. The gel is then washed with acetone (P.A. quality, May & Baker Ltd, Dagenham, England) to remove the water and is modified according to the procedure set forth in Example 1 above. This modified affinity gel is also vacuum-dried for long-term storage.

EXAMPLE 3

The modified affinity gels of Example 1 and 2 are analyzed for fluorine content according to the following procedure. A 0.8 mg sample of the gel (swollen in isopropanol) is suspended in 5 ml of 0.1 M ammonium bicarbonate. The suspension is incubated for one hour a 68° C. Twenty milliliters of a pH 5.2 buffer, composed of 0.96 M acetic acid, 0.75 M sodium hydroxide and 1.5 mM citric acid, is added to the incubated suspension.

A fluoride selective electrode (Orion Research Incorporated) is calibrated to 0.8 mg of the unmodified Sepharose CL-4B and Epoxy-activated Sepharose CL-6B gels (swollen in isopropanol). The gels are suspended in 25 ml of various mixtures of buffer and sodium bicarbonate containing known concentrations of potassium fluoride. The mixtures contained four parts of the above pH 5.2 buffer and one part of a 0.1 M sodium bicarbonate solution.

The fluoride concentration of each of the modified gels is measured by the fluoride selective electrode and a saturated Calomel® reference electrode at 22° C. while the gel mixtures are subjected to continuous stirring.

Both modified gels (swollen in isopropanol) normally contained approximately 0.3 mmoles of the substituted POF groups.

EXAMPLE 4

The modified gels can be tested for their ability to inactivate plasmin in the following manner. Human plasmin (EC 3.4.21.7, Mr 85,000) is prepared from pure Gluplasminogen (Biopool AB, Umeå, Sweden) by the addition of 0.1% streptokinase according to the procedure of Wiman. (Wiman, B. Methods in Enzymology, Lorand, L., ed., Vol. 80, Part C, pp. 395–408, Academic Press, New York). The plasmin stock solution is stored at −20° C. in 50% glycerol at a concentration of 2 mg/ml.

A 0.5 mM plasmin substrate solution is prepared in a pH 7.3 buffer composed of 0.05% (v/v) Tween 80, 0.15 M sodium chloride and 0.02 M disodium hydrogenphosphate/potassium dihydrogenphosphate. The plasmin substrate is D-a-amino butylylcyclohexyltyrosyl-lysyl-p-nitroanilide (But-CHT-Lys-pNA from Biopool AB, Umeå, Sweden).

A 50 μl aliquot of the human plasmin is added to 0.5 ml of the 0.5 mM plasmin substrate solution, and the mixture is incubated at 22° C. for approximately three minutes. The reaction is stopped by adding 100 μl of a 4 M sodium acetate buffer, pH 3.8. Absorbance is determined at 405 nm in a conventional spectrophotometer. The sodium acetate buffer is used as the blank.

As shown in FIG. 1, when plasmin is mixed with the control gel, approximately 90% of the plasmin activity remained after approximately one hour. Plasmin mixed with the modified Sepharose CL-4B gel displayed activity decreasing to approximately 35% over the period of approximately one hour. Plasmin mixed with the modified Sepharose CL-6B gel displayed activity which rapidly decreased to 0% within approximately thirty minutes.

The modified Epoxy-activated Sepharose CL-6B gel is found to be superior to the modified Sepharose CL-4B gel in inhibiting plasmin activity. The inferior binding capacity of the modified Sepharose CL-4B gel is probably due to the steric hindrance of the ligand causing impaired reaction with the active site of the enzyme.

It should be understood that the foregoing related only to a preferred embodiment of the present invention and that numerous modifications or alterations may be made without departing from the spirit and scope of the invention as set forth in the appended claims.

We claim:

1. A modified affinity gel for the binding of serine proteases comprising:

(a) an affinity gel matrix including hydroxyl groups, and (b) an organophosphorous compound coupled to said matrix at said hydroxyl groups, wherein the coupling of said organophosphorous compound to said affinity gel causes the modification of said affinity gel providing a specific ligand for the binding of serine proteases, said modified affinity gel having the following chemical formula:

Matrix-O-POX-OR wherein X is fluorine, P is phosphorous, O is oxygen, R is isopropyl alcohol, and the matrix is a hydrophilic affinity gel selected from the group consisting of 4% cross-linked agarose and 6% epoxy-activated cross-linked agarose.

2. A method for the modification of an affinity gel matrix, comprising the steps of:

(a) reacting a phosphoryl trihalide with said affinity gel matrix according to the following chemical equation:

$$\text{Matrix-OH} + POX_3 \rightarrow \text{Matrix-O-}POX_2 + HX$$

wherein the hydroxylated matrix is a hydrophilic affinity gel selected from the group consisting of 4% cross-linked agarose and 6% epoxy-activated cross-linked agarose $POX_2$ is a phosphoryl difluoride and X is fluorine so that the matrix is coupled to the phosphoryl difluoride; and (b) reacting said matrix coupled to said phosphoryl difluoride, with a sufficient amount of alcohol according to the following chemical equation:

$$\text{Matrix-O-}POX_2 + ROH \rightarrow \text{Matrix-O-POX-OR} + HX$$

wherein R is isopropyl alcohol, so that the matrix is coupled to an organophosphorous compound.

3. The method of claim 2, wherein said step of reacting said phosphoryl trifluoride with said hydrophilic affinity gel matrix comprises reacting said phosphoryl trifluoride with said hydrophilic affinity gel matrix for approximately at least three hours at a temperature below −50° C. and at a pressure below approximately 200 mm mercury.

4. The method of claim 3, wherein said step of reacting said matrix coupled to said phosphoryl difluoride comprises reacting said matrix with said isopropyl alcohol for approximately at least three hours at a temperature below approximately 25° C.

5. A method for removal of serine proteases from a biological sample, comprising the steps of:

(a) coupling an organophosphorous compound to a hydrophilic affinity gel matrix according to the following chemical equations:

$$\text{Matrix-OH} + POX_3 \rightarrow \text{Matrix-O-}POX_2 - HX$$

$$\text{Matrix-O-}POX_2 - ROH \rightarrow \text{Matrix-O-POX-OR} - HX$$

wherein the matrix is a hydrophilic affinity gel selected from the group consisting of 4% cross-linked agarose and 6% epoxy-activated cross-linked agarose X is fluorine and R is isopropyl alcohol, and (b) interacting said organophosphorous compound coupled to said affinity gel with said biological sample, wherein said gel covalently binds to said serine proteases in said biological sample.

* * * * *